United States Patent [19]

Mendise

[11] Patent Number: 5,148,940

[45] Date of Patent: Sep. 22, 1992

[54] APPARATUS AND METHOD FOR DISPOSING OF INFECTIOUS MEDICAL WASTE

[75] Inventor: Nicholas E. Mendise, Columbus, Miss.

[73] Assignee: Microtek Medical, Inc., Columbus, Miss.

[21] Appl. No.: 679,619

[22] Filed: Apr. 3, 1991

[51] Int. Cl.$^5$ .............................................. B65D 90/04
[52] U.S. Cl. .................................... 220/404; 220/908; 229/101; 229/125; 229/132; 206/459.5; 128/849; 604/317
[58] Field of Search ............... 220/403, 404, 908, 287, 220/62; 229/101, 125, 132; 206/44 R, 45.17, 216, 366, 459; 128/849, 852, 853, 854; 604/317

[56] References Cited

U.S. PATENT DOCUMENTS

| | | | |
|---|---|---|---|
| 1,677,654 | 7/1928 | Pitts | 206/44 K |
| 2,344,999 | 3/1944 | Newsom | 229/120.34 |
| 2,382,891 | 8/1945 | McCormick | 229/126 |
| 3,313,467 | 4/1967 | Anderskow et al. | 229/101 |
| 3,346,399 | 10/1967 | Watson et al. | 426/111 |
| 3,423,277 | 1/1969 | Dipner | 128/849 X |
| 3,443,971 | 5/1969 | Wood | 220/404 X |
| 3,482,567 | 12/1969 | Franklin | 128/849 |
| 3,494,356 | 2/1970 | Melges | 128/849 |
| 3,539,360 | 11/1970 | Wood | 220/403 |
| 3,576,290 | 4/1971 | Marchisen | 220/404 X |
| 3,598,303 | 8/1971 | Folz | 229/101 |
| 3,727,827 | 4/1973 | Stice | 229/101 |
| 3,788,876 | 1/1974 | Baker et al. | 229/132 |
| 4,518,115 | 5/1985 | Sedwick | 229/132 X |
| 4,534,489 | 8/1985 | Bartlett | 220/404 |
| 4,863,052 | 9/1989 | Lambert | 220/908 X |
| 4,886,164 | 12/1989 | Stein et al. | 206/366 |
| 4,890,628 | 1/1990 | Jackson | 128/849 |

FOREIGN PATENT DOCUMENTS 2612885  9/1988  France .................... 229/101

Primary Examiner—Stephen Marcus
Assistant Examiner—Stephen Cronin
Attorney, Agent, or Firm—Baker & Botts

[57] ABSTRACT

Apparatus and method for collecting, storing, transporting, and disposing of biohazardous medical waste material with minimum handling and reduced risk of cross-contamination. A liquid-tight plastic bag (96), disposable fluid collection drape (98), and other disposable items (100) used in a medical procedure are received at the point of use in a vertically expandable paperboard carton (11). During a medical procedure, the drape (98) is used to funnel liquid wastes into the waste receptacle (106) consisting of the opened carton (11) lined with the enclosed bag (96). At the conclusion of the procedure, the drape (98) and other waste materials are also disposed of in the receptacle (106). The bag (96) is sealed closed, left in the carton (11), and the carton (11) is the selectively closed and sealed to the appropriate size to accommodate the volume of wastes in the bag (96). The entire waste receptacle (106) remains sealed until disposed of.

7 Claims, 2 Drawing Sheets

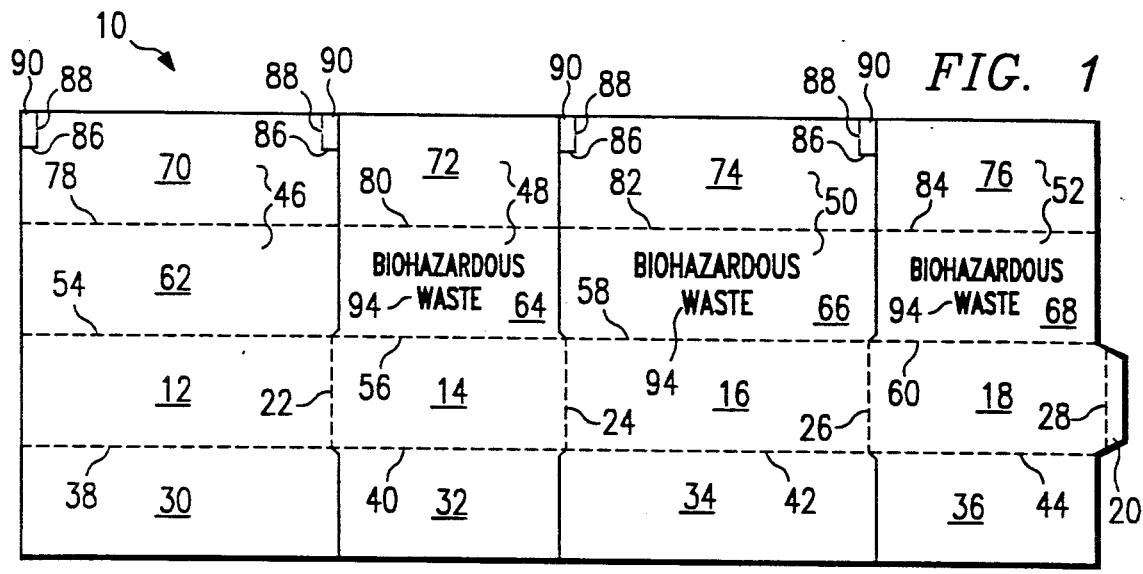
FIG. 1
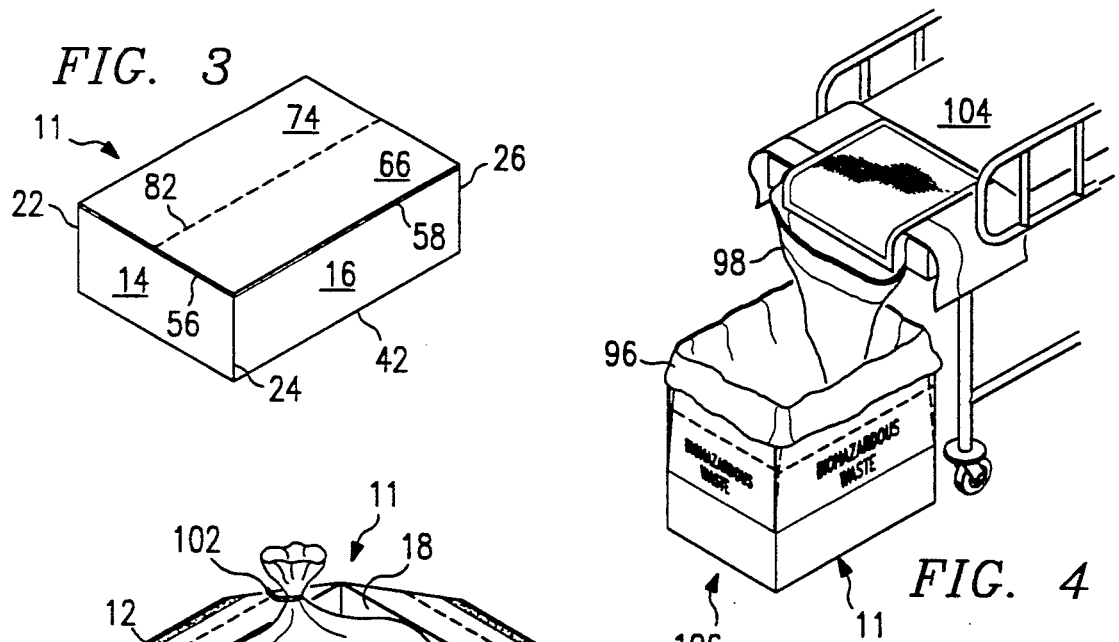
FIG. 3
FIG. 4
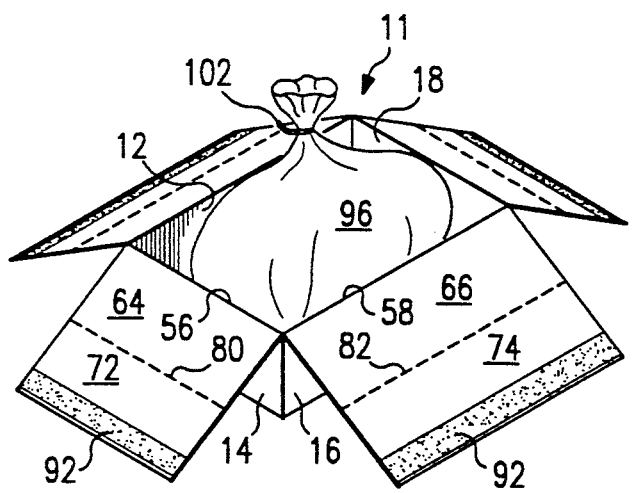
FIG. 5
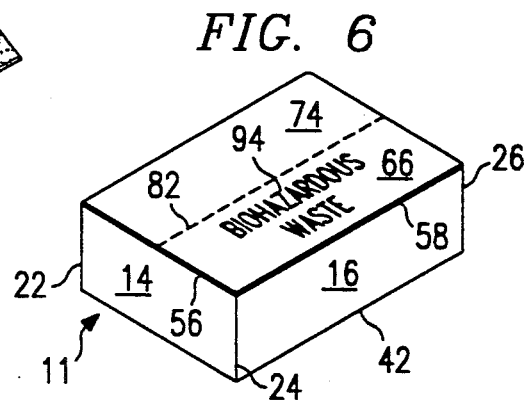
FIG. 6

APPARATUS AND METHOD FOR DISPOSING OF INFECTIOUS MEDICAL WASTE

TECHNICAL FIELD OF THE INVENTION

This invention generally relates to medical waste containers, and, more particularly, is concerned with an apparatus and method for collecting, transporting and disposing of biohazardous medical waste material of the type commonly generated in hospitals, physicians' offices and at other locations, with minimum handling and with reduced risk of cross-contamination.

BACKGROUND OF THE INVENTION

A wide variety of biohazardous and infectious medical waste materials are generated in hospitals, doctors' offices, veterinarians' offices, research facilities, and the like. These waste materials include items of dry or semi-solid material such as pathological wastes, blood supply paraphernalia, dressings, gloves, gowns, and blood-soaked linen, and further include liquid wastes such as blood plasma, body fluid specimens, and discarded vaccines. The waste materials also include sharp items, such as hypodermic needles, syringes, blood vials, scalpel blades, culture dishes, and broken and unbroken glassware that were in contact with infectious agents. The risk of cross-contamination and infection from these waste materials prior to their ultimate disposal is well known. In recent years, the additional risk of infection with the AIDS virus has intensified the need for a method of disposing of medical wastes with minimum risk of cross-contamination.

Generators and transporters of medical wastes are also becoming increasingly subject to federal regulation. Environmental Protection Agency regulations promulgated pursuant to the Medical Waste Tracking Act of 1988 established a pilot program within four states and Puerto Rico for the handling, packaging, labeling, storing, and transportation of regulated medical wastes. 40 CFR § 259. Under these regulations, containers for medical wastes must be rigid, leak-resistant, impervious to moisture, sealed to prevent leakage during transport, and of sufficient strength to prevent tearing or bursting under normal conditions of use and handling. 40 CFR § 259.41. Packaging for sharps and sharps with residual fluids are required to be puncture resistant. It is anticipated that these or similar regulations may in the future be imposed on all generators and handlers of medical wastes nationwide.

Medical waste materials have typically been disposed of by discarding them into plastic bags generally supported by receptacles such as trash cans. When filled, the bags are closed, removed from the support receptacles, and set aside until either transported to a disposal facility, or disposed of on site, as by incineration. More recently, specialized rigid containers have been proposed as an alternative to plastic bags. One form of such container is a plastic box with a hinged snap over or snap down lid, as disclosed by Pepper in U.S. Pat. No. 4,488,643; Nelson et al in U.S. Pat. No. 4,494,652; and Shillington et al in U.S. Pat. No. 4,454,944. Other proposed rigid containers consist of corrugated paperboard cartons lined internally with one or more plastic bags. For example, Bartlett in U.S. Pat. No. 4,534,489 discloses a bag-lined paperboard carton with a pivoted single-piece lid. Stein, in U.S. Pat. No. 4,886,164, discloses a bag-lined corrugated paper box that is closed by a separate corrugated paper insert.

While these prior devices may be somewhat effective as a means of sanitarily disposing of medical wastes, they suffer from several inherent disadvantages. The plastic bags alone are subject to being punctured by any sharp waste items, such as hypodermic needles or scalpel blades, they may contain. In addition, they are subject to being punctured or torn by external objects during handling and transportation. The rigid containers, although less subject to puncture and leakage, require large amounts of storage and transportation space, both before and after use, due to their fixed volumes. When the fixed volume rigid containers are only partially filled with liquid, shifting of the liquid can cause handling and transit problems. The plastic containers are generally not biodegradable, and thus create a waste disposal problem of their own. The prior paperboard containers have been of a complicated and intricate design, requiring extensive retooling over and above that used in more conventional cardboard containers. These containers also require separate components, such as inserts, sleeves, or fastening pins, to close and seal them. Finally, the prior rigid containers have been relatively expensive, particularly in view of their one-time use.

Consequently, a need exists for a low-cost liquid-tight medical waste container that is puncture and tear resistant, simply and quickly closed, and does not require excessive amounts of space during storage and transportation.

SUMMARY OF THE INVENTION

The present invention provides a "completely closed" system for the collection, storage, transportation, and disposal of biohazardous medical waste material which answers the aforementioned needs. According to the invention, there is provided a disposable, multi-volume but rigid, receptacle for collection, containment, storage and transportation of biohazardous waste material. The receptacle outer container is formed from a unitary sheet or blank of semi-rigid material, such as corrugated paperboard. When constructed, the container has a rectangular body with two sides and two end wall panels, and a multi-ply bottom, in the conventional manner of a corrugated paperboard carton. The multi-volume feature of the container resides in the design of the closure flaps at its top. These flaps are provided with both lower fold lines at their connections to the side or end wall panels, and upper fold lines approximately midway between these connections and the opposite ends of each flap. When the closure flaps are folded at the lower fold lines, the closed container assume a vertically contracted size. When the flaps are folded at their upper fold lines, the lower parts of the closure flaps form vertical extensions of the side and end wall panels, and the closed container assumes a vertically expanded size. A third, still further expanded size is provided for the open container when the closure flaps are opened and erected to form upstanding extensions of the side and end wall panels.

The invention provides for the above described containers to be shipped to the user in their contracted closed size, for conservation of shipping and storage space. Shipped inside each container is a red, flexible, liquid-tight disposable plastic bag that is used as a liner for the waste receptacle. Shipped inside the bag are a disposable fluid collection drape and other disposable components used in a medical procedure, such as surgical sponges and gauze pads. An appropriate cautionary legend or symbol, such as the words "BIOHAZARDOUS WASTE," is either printed on the outside of the container, or is provided on an adhesive label for attachment to the container at the time of use.

According to the invention, when a waste receptacle is needed by medical personnel beginning a procedure, the container is opened and the closure flaps are fully erected. The plastic bag is opened and its upper edges are bloused over the upper edges of the upstanding closure flaps, thus presenting a large volume, liquid-tight, rigid receptacle for receiving waste materials. The fluid collection drape and other components are removed from the bag. During the procedure, the drape is used to funnel wastes directly into the receptacle. At the conclusion of the procedure, the drape and other disposable waste materials are disposed of in the receptacle. The plastic bag is then closed and sealed. The outer container of the receptacle is then closed to either its expanded or its contracted size, depending on the volume of waste material to be accommodated. Self-adhesive strips are provided on the insides of the closure flaps to secure the outer container closed.

The waste receptacle of the present invention thus achieves the advantages found in each of the previously available disposal devices, but without their attendant disadvantages. The inventor's receptacle has the rigidity and puncture and tear resistance of a fixed-volume rigid container, yet it also has the multiple-volume feature associated with less rigid containers, such as plastic bags. The receptacle is quickly and easily closed and sealed without the need for separate components or fasteners. The entire receptacle is biodegradable. Finally, the receptacle is simple and relatively inexpensive to manufacture in comparison to prior rigid disposal containers.

BRIEF DESCRIPTION OF THE DRAWINGS

For a more complete understanding of the present invention, and the advantages thereof, reference is now made to the following description of the Preferred Embodiment, taken in conjunction with the accompanying drawings, in which:

FIG. 1 is a plan view of a cut and scored corrugated paperboard blank from which a preferred embodiment of the outer container of this invention is formed.

FIG. 3 is a perspective view of the outer container of FIG. 2, shown closed to its contracted size, as it is shipped and stored prior to use.

FIG. 4 is a perspective view of the open waste receptacle of this invention and the fluid collection drape as they might be used during a medical procedure.

FIG. 5 is a perspective view of the receptacle of FIG. 4 after the bag has been filled and closed, but before the outer container has been closed.

FIG. 6 is the receptacle of FIG. 4 after the outer container has been closed to its contracted size.

DETAILED DESCRIPTION OF THE INVENTION

Figure 2:
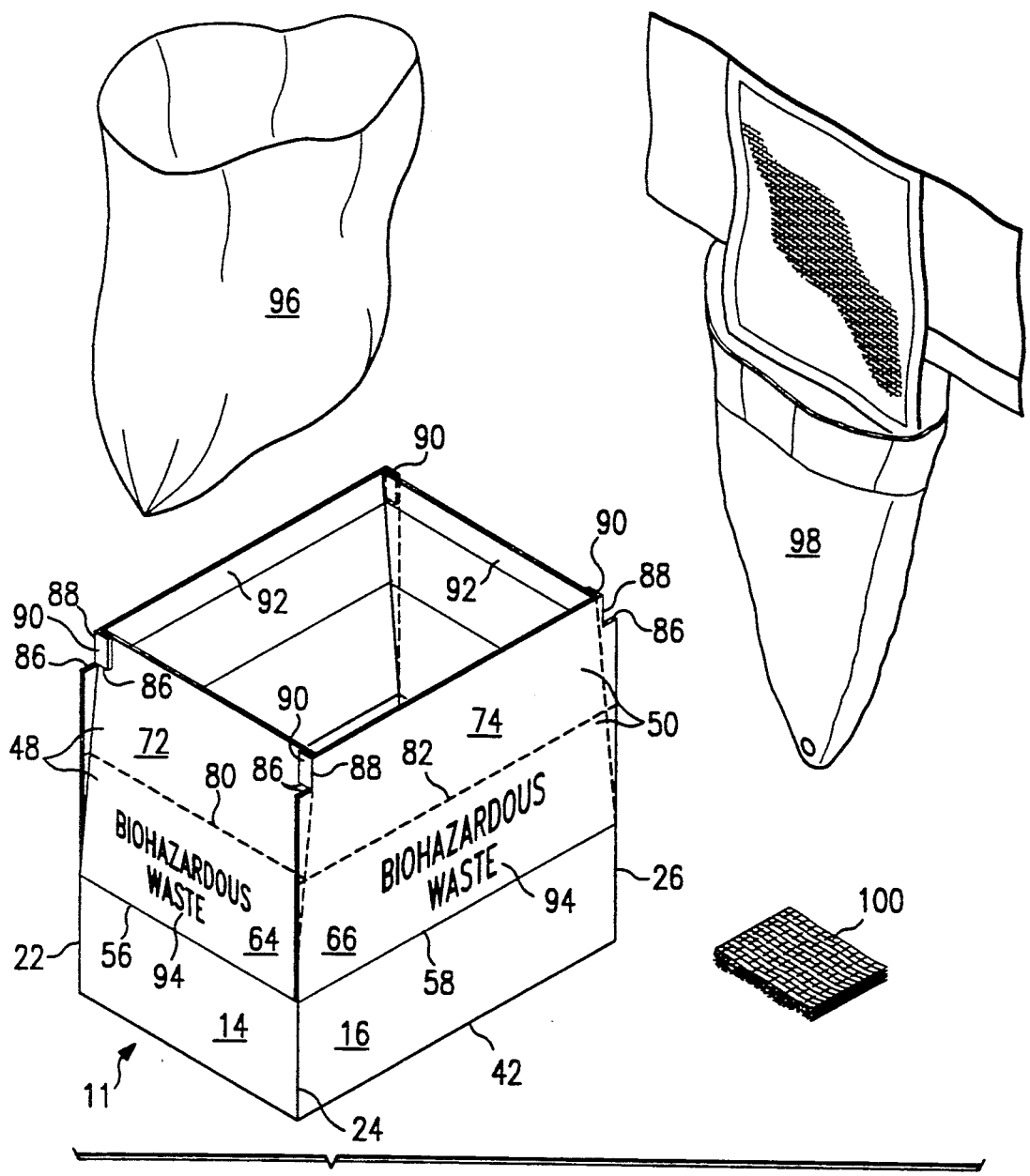
FIG. 2 is a perspective view of the outer container of the receptacle of this invention, shown with its closure flaps erected, together with the plastic bag, fluid collection drape, and disposable gauze pads associated with this invention.

The preferred embodiment of the present invention and its advantages are best understood by referring to the drawings, like numerals being used for like and corresponding parts of the various drawings.

In FIG. 1 there is shown, in plan view, a cut and scored double walled corrugated paperboard blank 10 from which is constructed the outer container of the receptacle of this invention. The blank 10 includes a pair of side wall panels 12 and 16 and a pair of end wall panels 14 and 18 which are interconnected by fold lines 22, 24, and 26. The end wall panel 18 includes a securement flap 20 connected thereto by a fold line 28. Bottom wall panels 30 and 34 are connected to side wall panels 12 and 16, respectively, by fold lines 38 and 42, respectively, and bottom wall panels 32 and 36 are connected to end wall panels 14 and 18, respectively, by fold lines 40 and 44, respectively. Closure flaps 46 and 50 are connected to side wall panels 12 and 16, respectively, by fold lines 54 and 58, respectively, and closure flaps 48 and 52 are connected to end wall panels 14 and 18, respectively, by fold lines 56 and 60, respectively. Closure flaps 46, 48, 50 and 52 are each divided into an inner closure flap panel 62, 64, 66 and 68, respectively, and an outer closure flap panel 70, 72, 74 and 76, respectively, by an auxiliary fold line 78, 80, 82 and 84, respectively. Outer closure flap panels 70 and 74 each have two small cuts 86 extending to relatively short fold lines 88 which form securement flaps 90 at the free corners of panels 70 and 74. The free outer edges of the securement flaps 90 face toward outer closure flap panels 72 or 76, neither of which panels have such securement flaps 90.

The container 11 is erected by first folding the blank 10 about fold lines 22, 24, and 26 to form a rectangular tubular body from side wall panels 12 and 16 and end wall panels 14 and 18, Securement flap 20 is then permanently attached to the interior surface of side wall panel 12 by glue or staples (not shown). Bottom wall panels 32 and 36 are then folded so as to partially close the container bottom, and bottom wall panels 30 and 34 are then folded over panels 32 and 36, overlappingly, so as to completely close the bottom of container 11. Bottom wall panels 30 and 34 are then permanently secured into their closed position by a strip of sealing tape (not shown), in the conventional manner for closing and sealing the bottom of a paperboard carton. FIG. 2 shows the container 11 as thus erected and closed on its bottom.

As also shown in FIG. 2, a self-adhesive strip 92 is applied to the interior surface of outer closure flap panels 70, 72, 74 and 76, at their outer free edges. In the case of panels 70 and 74, the self-adhesive strips 92 extend onto and cover essentially the entire surface of the securement flaps 90. Each self-adhesive strip 92 is covered by a strippable protective film (not shown) that is peeled off when the top of the container 11 is to be secured closed.

The container 11 preferably has a white or off-white colored exterior surface which can be printed upon, and a moisture resistant coated interior surface. An appropriate cautionary legend or symbol 94, such as "BIOHAZARDOUS WASTE" or the universal biohazard symbol, is printed on inner closure flap panels 64, 66 and 68 only. No cautionary legend is printed on flap panel 62, for reasons that will become apparent hereafter.

Alternatively, the cautionary legends may be provided on detached self-adhesive labels (not shown), to be affixed to container 11 at the time of use.

FIG. 2 also illustrates the disposable bag 96 and disposable fluid collection drape 98 which are additional components of this invention, and which may be stored within the initially closed container 11. Also shown are gauze pads 100, which are representative of disposable soft goods used in a medical procedure than may also be included as part of the invention. The bag 96 is of fluid-tight flexible plastic material, preferably 2 to 4 mil polyethylene, of red color, and appropriately sized to serve as a liner for container 11 when fitted therein.

Before shipment to the user of the waste receptacle, the container 11 is erected and closed on its bottom as described above. The drape 98 and other disposable goods 100 are placed in the bag 96, and the bag 96 is placed in the container 11. Closure flaps 48 and 52 are then folded over at fold lines 56 and 60, respectively, so as to close the top of container 11. Closure flap 50 is then folded down at fold line 58, overlapping closure flaps 48 and 52. Finally, closure flap 46 is folded down at fold line 54, overlapping flap 50. FIG. 3 shows container thus closed, and as it is shipped to the user and stored until used. It should be noticed that, when closed in this manner, container 11 assumes a vertically contracted size, which conserves space during transit and storage prior to use. In addition, when closure flaps 46, 48, 50 and 52 are closed in the above described sequence, the cautionary legends printed on closure flap panels 64, 66, and 68 are covered by unprinted flap 46, and therefore unused containers 11 will not be confused with or mistaken for containers holding medical wastes destined for disposal.

Referring again to FIG. 2, when medical personnel begin a procedure in which waste material will be generated, closure flaps 46, 48, 50, and 52 of container 11 are opened, and the drape 98 and other disposable components 100 are removed from bag 96. Closure flaps 46, 48, 50, and 52 are erected to form vertical extensions of side wall panels 12 and 16 and end wall panels 14 and 18, respectively. The protective film (not shown) is peeled back from the self-adhesive strips 92 on securement flaps 90 on the outer corners of closure flaps 46 and 50. The protective film is left attached to the remainder of the self-adhesive strips on flaps 46 and 50. Securement flaps 90 are then folded over at fold lines 88, and adhesively attached to the upper corners of adjacent closure flaps 48 and 52. The four closure flaps 46, 48, 50, and 52 are thus securely attached together to make a sturdy receptacle 106.

Referring now to FIG. 4, the upper edge of bag 96 is then bloused over the upper edges of closure flaps 46, 48, 50 and 52. The upper end of drape 98 is positioned on the procedure table 104, and receptacle 106 is positioned under the bottom of drape 98. During the procedure, the drape 98 is used to funnel liquid wastes directly into the receptacle 106. At the conclusion of the procedure, the drape 98 and other disposable components 100 are disposed of in the receptacle 106.

Referring now to FIG. 5, the bag 96 is then closed and sealed with a twist-tie closure 102 which is provided. The securement flaps 90 on closure flaps 46 and 50 are detached from closure flaps 48 and 52 by breaking the adhesive. The protective film covering self-adhesive strips 92 on each of closure flaps 46, 48, 50, and 52 is removed entirely. The container 11 is then closed to one of its two closed sizes.

If bag 96 contains a relatively small volume of waste, closure flaps 48 and 52 are folded down at their lower fold lines 56 and 60, respectively, where they connect to end wall panels 14 and 18, respectively. Closure flap 46 is then folded down at its lower fold line 54, where it connects to side wall panel 12, overlapping and sealing to closure flaps 48 and 52. Finally, closure flap 50 is folded down at fold line 58, where it connects to side wall panel 16, overlapping and sealing to flap 46. FIG. 6 shows container 11 thus closed to its vertically contracted size. It should be noticed that, when the closure flaps 46, 48, 50, and 52 are closed in this sequence, the cautionary legend 94 printed on closure flap 50 is visible.

Figure 7:
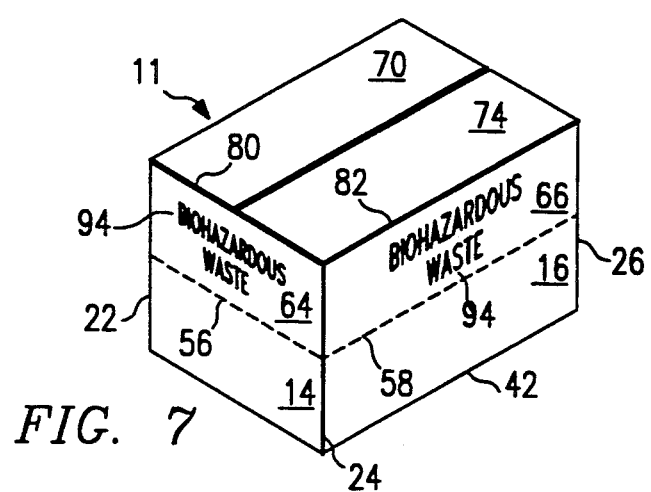
FIG. 7 is the receptacle of FIG. 4 after the outer container has been closed to its expanded size.

If bag 96 is relatively full of waste material when it is closed, container 11 is instead closed to its vertically expanded size to accommodate the larger volume. This is accomplished by first folding down only the outer flap panels 72 and 76 of closure flaps 48 and 52, respectively, at their auxiliary fold lines 80 and 84, respectively. The inner flap panels 64 and 68 of closure flaps 48 and 52, respectively, thus remain upright, forming vertical extensions of end wall panels 14 and 18, respectively. Outer flap panel 70 of closure flap 46 is then folded down at its auxiliary fold line 78, partially overlapping and sealing to outer flap panels 72 and 76 of closure flaps 48 and 52, respectively, and leaving inner flap panel 62 standing as a vertical extension of side wall panel 12. Finally, outer flap panel 74 of closure flap 50 is folded down at its auxiliary fold line 82, overlapping and sealing to the exposed sides of outer flap panels 72 and 76 of closure flaps 48 and 52, respectively, and leaving inner flaps panel 66 standing as an extension of side wall panel 16. FIG. 7 shows container 11 thus closed to its vertically expanded size. It should be noticed that the cautionary legends 94 printed on flaps 48, 50, and 52 are visible when container 11 is closed in this manner.

Therefore, regardless of whether container 11 is closed to its contracted or its expanded size, it is properly sealed and marked with a cautionary legend 94, and ready for ultimate disposal, as by incineration. Because bag 96 is never removed from container 11, handling and risk of cross-contamination are minimized by use of the receptacle of this invention. It will be appreciated that this invention provides a puncture and tear resistant, sturdy, mobile, multi-volume and yet completely disposable medical waste container which is particularly suited for use in hospitals, clinics, laboratories, veterinarian's offices, and in other locations which produce biohazardous waste material.

It will also be appreciated that the container of this invention can be modified to provide three or more closed sizes, by simply adding additional auxiliary fold lines to closure flaps 46, 48, 50, and 52. This invention is therefore not limited to a two-sized container as above described.

The same receptacle 106 design, with changes only in the cautionary legend 94 and the material of bag 96, can also be used for the collection, storage, transportation, and disposal of low level radioactive wastes generated by hospital nuclear medicine departments.

The infectious medical waste disposal apparatus and method of the present invention, and many of its intended advantages, will be understood from the foregoing description and it will be apparent that, although the invention and its advantages have been described in detail, various changes, substitutions, and alterations may be made in the manner, procedure, and details thereof without departing from the spirit and scope of the invention, as defined by the appended claims, or sacrificing all of its material advantages, the form hereinbefore described being merely a preferred or exemplary embodiment thereof.

What is claimed is:

1. A vertically contractible and expandable disposable receptacle for collection, containment, storage, and transportation of waste material, said receptacle comprising:
    an outer container formed from semi-rigid material, said material being cut and creased to provide;
        a pair of side wall panels and a pair of end wall panels hingedly connected together and foldable along fold lines to form a rectangular container body;
        at least one bottom wall panel foldably connected to a bottom edge, of at least one of said side wall or end wall panels to form a bottom for said receptacle;
        a plurality of closure flaps hingedly connected at fold lines to the upper edges of at least two of said side wall or end wall panels and overlappingly disposed to form a multi-ply closure for said receptacle, each of said closure flaps being divided by an auxiliary fold line parallel to said fold line connecting said closure flaps to said side or end wall panels, whereby said receptacle can be closed into a vertically contracted size by folding said closure flaps at the fold lines joining said flaps to said side or end wall panels, or into a vertically expanded size by folding said closure flaps at said auxiliary fold lines in said flaps, and whereby said closure flaps may be erected to form upstanding extensions of said side or end wall panels;
    a bag of flexible material disposed in the outer container, said bag having an opened shape complimentary to the interior of said outer container when said closure flaps are so erected and upstanding, and whereby the marginal edges of the opening of said bag may be bloused over the upper edges of said closure flaps when said flaps are so erected and upstanding; and
    means for removably securing said closure flaps together when said closure flaps are erected to form upstanding extensions of said side and end wall panels.

2. The receptacle of claim 1, wherein said means for removably securing said closure flaps together comprises a securement flap foldably connected to at least one of said closure flaps, said securement flap foldably overlying and attaching to the surface of an adjacent closure flap when said closure flaps are erected to form upstanding extensions of said side and end wall panels.

3. The receptacle of claim 2, wherein said securement flaps are located on opposite sides of two of said closure flaps on opposite sides of said outer container.

4. The receptacle of claim 3, further including a self-adhesive strip covered by a strippable protective film extending across the interior surface of at least one of said closure flaps and along its free edge, for securing said flaps together when said receptacle is closed, and wherein said securement flaps are located at the free edges of said closure flaps, whereby said self-adhesive strip on said interior surface of said closure flap extends onto the interior surface of each said securement flap, and whereby said securement flaps may be attached to said outer surfaces of adjacent closure flaps by said self-adhesive strips on said securement flaps.

5. A vertically contractible and expandable disposable receptacle for collection, containment, storage, and transportation of waste material, said receptacle comprising:
    an outer container formed from semi-rigid material, said material being cut and creased to provide:
        a pair of side wall panels and a pair of end wall panels hingedly connected together and foldable along fold lines to form a rectangular container body;
        at least one bottom wall panel foldably connected to a bottom edge of at least one of said side wall or end wall panels to form a bottom for said receptacle;
        a plurality of closure flaps hingedly connected at fold lines to the upper edges of at least two of said side wall or end wall panels and overlappingly disposed to form a multi-ply closure for said receptacle, each of said closure flaps being divided by an auxiliary fold line parallel to said fold line connecting said closure flaps to said side or end wall panels, whereby said receptacle can be closed into a vertically contracted size by folding said closure flaps at the fold lines joining said flaps to said side or end wall panels, or into a vertically expanded size by folding said closure flaps at said auxiliary fold lines in said flaps, and whereby said closure flaps may be erected to form upstanding extensions of said side or end wall panels;
    a bag of flexible material disposed in the outer container, said bag having an opened shape complimentary to the interior of said outer container when said closure flaps are so erected and upstanding, and whereby the marginal edges of the opening of said bag may be bloused over the upper edges of said closure flaps when said flaps are so erected and upstanding; and
    a disposable fluid collection drape for conveying waste material into said bag, said drape being disposed within said bag prior to use of said drape and receptacle.

6. A vertically contractible and expandable disposable receptacle for collection, containment, storage, and transportation of waste material, said receptacle comprising:
    an outer container formed from semi-rigid material, said material being cut and creased to provide:
        a pair of side wall panels and a pair of end wall panels hingedly connected together and foldable along fold lines to form a rectangular container body;
        at least one bottom wall panel foldably connected to a bottom edge of at least one of said side wall or end wall panels to form a bottom for said receptacle;
        a plurality of closure flaps hingedly connected at fold lines to the upper edges of at least two of said side wall of end wall panels and overlappingly disposed to form a multi-ply closure for said receptacle, each of said closure flaps being divided by an auxiliary fold line parallel to said fold line connecting said closure flaps to said side or end wall panels, whereby said receptacle can be closed into a vertically contracted size by folding said closure flaps at the fold lines joining said flaps to said side or end wall panels, or into a vertically expanded size by folding said closure flaps at said auxiliary fold lines in said flaps, and whereby said closure flaps may be erected to form upstanding extensions of said side or end wall panels;

a bag of flexible material disposed in the outer container, said bag having an opened shape complimentary to the interior of said outer container when said closure flaps are so erected and upstanding, and whereby the marginal edges of the opening of said bag may be bloused over the upper edges of said closure flaps when said flaps are so erected and upstanding; and a plurality of disposable surgical sponges and gauze pads, said sponges and pads being disposed within said bag prior to use of said sponges, pads and receptacle.

7. A vertically contractible and expandable disposable receptacle for collection, containment, storage, and transportation of waste material, said receptacle comprising:

an outer container formed from semi-rigid material, said material being cut and creased to provide;

a pair of side wall panels and a pair of end wall panels hingedly connected together and foldable along fold lines to form a rectangular container body;

at least one bottom wall panel foldably connected to a bottom edge of at least one of said side wall or end wall panels to form a bottom for said receptacle;

a plurality of closure flaps hingedly connected at fold lines to the upper edges of at least two of said side wall or end wall panels and overlappingly disposed to form a multi-ply closure for said receptacle, each of said closure flaps being divided by an auxiliary fold line parallel to said fold line connecting said closure flaps to said side or end wall panels whereby said receptacle can be closed into a vertically contracted size by folding said closure flaps at the fold lines joining said flaps to said side or end wall panels, or into a vertically expanded size by folding said closure flaps at said auxiliary fold lines in said flaps, and whereby said closure flaps may be erected to form upstanding extensions of said side or end wall panels;

a bag of flexible material disposed in the outer container, said bag having an opened shape complimentary to the interior of said outer container when said closure flaps are so erected and upstanding, and whereby the marginal edges of the opening of said bag may be bloused over the upper edges of said closure flaps when said flaps are so erected and upstanding; and wherein the outer surface of at least one of said closure flaps bears an appropriate cautionary legend or symbol, and whereby said legend is selectively exposed or concealed when said receptacle is closed to said contracted size, depending on the order in which said closure flaps are overlappingly folded, and whereby said legend is exposed when said receptacle is closed to said expanded size.

* * * * *

UNITED STATES PATENT AND TRADEMARK OFFICE
CERTIFICATE OF CORRECTION

PATENT NO. : 5,148,940

DATED : September 22, 1992

INVENTOR(S) : Nicholas E. Mendise

It is certified that error appears in the above-identified patent and that said Letters Patent is hereby corrected as shown below:

Column 1, line 48, after "resistant.", insert -- Id. --.

Column 4, line 43, after "container", insert -- 11 --.

Column 7, line 13, after "provide", delete " ; " and insert -- : --.

Column 7, line 19, after "edge", delete " ; ".

Column 9, line 25, after "provide", delete " ; " and insert -- : --.

Line 15 of abstract, after "is", delete "the" and insert -- then --.

Signed and Sealed this

Fourteenth Day of September, 1993

Attest:

BRUCE LEHMAN

Attesting Officer

Commissioner of Patents and Trademarks